US006255250B1

(12) United States Patent
Finch et al.

(10) Patent No.: US 6,255,250 B1
(45) Date of Patent: Jul. 3, 2001

(54) PLANT GROWTH REGULATORS IN PYRROLIDONE SOLVENTS

(75) Inventors: Charles W. Finch, Garner; Donna Zormeier, Raleigh, both of NC (US)

(73) Assignee: BASF Corporation, Mt. Olive, NJ (US)

( * ) Notice: Subject to any disclaimer, the term of this patent is extended or adjusted under 35 U.S.C. 154(b) by 0 days.

(21) Appl. No.: 08/995,262

(22) Filed: Dec. 19, 1997

Related U.S. Application Data

(63) Continuation-in-part of application No. 08/771,768, filed on Dec. 20, 1996, now abandoned.

(51) Int. Cl.[7] .......................... A01N 37/00; A01N 37/02; A01N 37/14; A01N 43/36

(52) U.S. Cl. ......................... 504/138; 504/141; 504/147; 504/182; 504/287; 504/319; 504/320; 71/DIG. 1

(58) Field of Search .................................... 504/319, 320, 504/138, 141, 147, 182, 287; 71/DIG. 1

(56) References Cited

U.S. PATENT DOCUMENTS

| | | |
|---|---|---|
| 3,787,198 | 1/1974 | Hagimoto et al. .................. 504/134 |
| 3,876,782 | 4/1975 | Kishino et al. ..................... 514/113 |

(List continued on next page.)

FOREIGN PATENT DOCUMENTS

| | | |
|---|---|---|
| 0 322 583 | 7/1989 | (EP) . |
| 0 077078 A1 | 4/1993 | (EP) . |
| 2 566 626 A1 | 6/1984 | (FR) . |
| WO 96/18296 | 6/1996 | (WO) . |
| WO 88/00184 | 1/1998 | (WO) . |

OTHER PUBLICATIONS

Abeles; "Abscission: Role of Cellulase"; (1969) 44:447–452; *Plant Physiol.*

Amagasa, et al.; "The Mode of Flower–Inhibiting Action of Ethylene in Pharbitis nil"; (1987) 28(6):1159–1161; *Plant Cell Physiol.*

Atsmon, et al; "Comparative of effects gibberellin, silver nitrate and aminoethoxyvinyl glycine on sexual tendency and ethylene evolution in the cucumber plant"; (1979) 20(8):1547–1555; *Plant and Cell Physiol.*

BASF Corporation; "Pix® plant regulator—Results in Cotton (Southwest)"; (1987); *Technical Information Bulletin No. 8626.*

Beyer, et al; "Abscission: The Role of Ethylene Modification of Auxin Transport"; (1971) 48:208–212; *Plant Physiol.*

Cockshull, et al.; "2–Chloroethylphosphonic acid and flower initiation by Chrysanthemum morifolium Ramat, in short days and in long days"; (1978) 53:85–90; *Journal of Horticultural Science.*

Gianfagna, et al; "Mode of action and use of plant growth retardants in reducing the effects of environmental stress on horticultural crops"; (1992) 778–787; *Plant Growth Regulation.*

Grossmann, et al; "Inhibition of Ethylene Production in Sunflower Cell Suspensions by a Novel Oxime Ether Derivative"; (1991) 10:163–166; *Journal of Plant Growth Regulation.*

Guinn; "Abscission of Cotton Floral Buds and Bolls as Influenced by Factors Affecting Photosynthesis and Respiration"; (1974) 14:291–293; *Crop Science.*

Guinn; "Effects of Some Organic Solvents on Ethylene Evolution From Young Cotton Bolls"; (1977) 60:446–448; *Plant Physiol.*

Guinn; "Fruit Age and Changes in Abscisic Acid Content, Etylene Production, and Abscission Rate of Cotton Fruits"; (1982) 69:349–353; *Plant Physiol.*

Guinn; "Hormonal Relations in Flowering, Fruiting, and Cutout"; 265–272; *Western Cotton Research Laboratory* (No Date Available).

Guinn; "Nutritional Stress and Ethylene Evolution by Young Cotton Bolls"; (1976) 16:89–91; *Crop Science.*

Hoffmann; "Use of plant growth regulators in arable crops: Survey and outlook"; (1992) 798–808; *Progress in Plant Growth Regulation.*

Kirchner, et al; "Effects of novel oxime ether derivatives of aminooxyacetic acid on ethylene formation in leaves of oilseed rape and barley and on carnation flower senescence"; (1993) 13:41–46; *Plant Growth Regulation.*

(List continued on next page.)

*Primary Examiner*—John Pak

(57) ABSTRACT

Provided herein is a composition comprising a plant growth regulator, octylpyrrolidone, and an emulsifier. The composition may be provided with a plant growth regulator comprises a substituted oxime-ether of the formula:

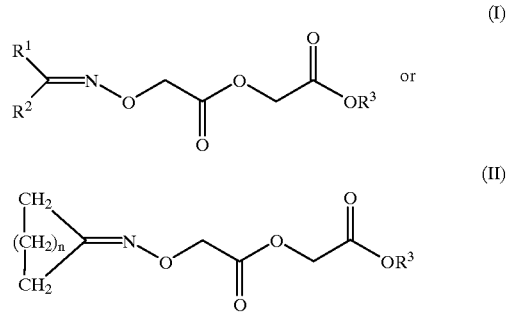

where R1 and R2 independently of one another are C1–C6-alkyl, n is 2 or 3 and R3 is hydrogen or C1–C6-alkyl. The compositions provided may also contain a blend of nonyl phenol ethoxylate and dioctyl sulfosuccinate. Also provided are methods of making the above compositions.

24 Claims, No Drawings

U.S. PATENT DOCUMENTS

| | | | |
|---|---|---|---|
| 3,894,123 | 7/1975 | Kishino et al. | 558/174 |
| 3,928,586 | 12/1975 | Sledzinski et al. | 514/136 |
| 3,970,728 | 7/1976 | Kishino et al. | 558/185 |
| 4,002,458 | 1/1977 | Hofacker | 71/27 |
| 4,124,227 | 11/1978 | Ruis | 503/224 |
| 4,181,715 | 1/1980 | Kondo et al. | 424/122 |
| 4,191,555 * | 3/1980 | Kliegman | 504/283 |
| 4,217,130 | 8/1980 | Tsurata et al. | 504/287 |
| 4,220,464 | 9/1980 | Martin | 504/312 |
| 4,227,918 | 10/1980 | Hofer et al. | 504/350 |
| 4,277,364 | 7/1981 | Shasha et al. | 56/10.8 |
| 4,344,857 | 8/1982 | Shasha et al. | 504/244 |
| 4,347,372 | 8/1982 | Fory et al. | 548/217 |
| 4,382,813 | 5/1983 | Shasha | 504/220 |
| 4,388,464 | 6/1983 | Kristinsson et al. | 548/136 |
| 4,461,638 | 7/1984 | Rajadhyasksha | 71/27 |
| 4,486,218 | 12/1984 | Reiser et al. | 548/262 |
| 4,531,964 | 7/1985 | Shimano et al. | 548/302 |
| 4,534,783 | 8/1985 | Beestman | 71/27 |
| 4,561,880 | 12/1985 | Shimano et al. | 548/264 |
| 4,563,212 | 1/1986 | Becher et al. | 71/11 |
| 4,594,099 | 6/1986 | Yamada et al. | 548/513 |
| 4,640,709 | 2/1987 | Beestman | 504/300 |
| 4,647,302 | 3/1987 | Reiser et al. | 514/383 |
| 4,659,722 | 4/1987 | Nakagawa et al. | 514/332 |
| 4,690,934 | 9/1987 | Yoshida et al. | 514/354 |
| 4,715,883 | 12/1987 | Lukaszczyk et al. | 504/106 |
| 4,719,287 | 1/1988 | Login et al. | 530/317 |
| 4,729,783 | 3/1988 | Regel et al. | 514/383 |
| 4,743,293 | 5/1988 | Reiser et al. | 548/262 |
| 4,744,811 | 5/1988 | Schulz et al. | 504/319 |
| 4,749,405 | 6/1988 | Reiser et al. | 514/184 |
| 4,775,527 | 10/1988 | Bires et al. | 424/62 |
| 4,785,048 | 11/1988 | Chao | 427/146 |
| 4,793,994 | 12/1988 | Helioff et al. | 424/70.4 |
| 4,804,762 | 2/1989 | Yoshida et al. | 514/336 |
| 4,851,035 | 7/1989 | Pirrung et al. | 504/320 |
| 4,871,766 | 10/1989 | Tsuda et al. | 514/521 |
| 4,911,952 | 3/1990 | Doane et al. | 427/213.31 |
| 4,923,503 | 5/1990 | Schulz et al. | 504/274 |
| 4,936,901 | 6/1990 | Surgant et al. | 504/133 |
| 4,956,129 | 9/1990 | Scher et al. | 264/4.7 |
| 4,997,642 | 3/1991 | Curtis et al. | 424/681 |
| 5,024,937 | 6/1991 | Penticoff et al. | 435/41 |
| 5,037,716 | 8/1991 | Moffat | 430/109 |
| 5,069,711 | 12/1991 | Fischer et al. | 504/246 |
| 5,078,888 | 1/1992 | Penticoff et al. | 210/639 |
| 5,087,456 | 2/1992 | Meinard et al. | 424/501 |
| 5,089,046 | 2/1992 | Lee et al. | 504/207 |
| 5,093,031 | 3/1992 | Login et al. | 516/68 |
| 5,125,959 | 6/1992 | Suyama et al. | 504/253 |
| 5,126,360 | 6/1992 | Dutzmann et al. | 514/383 |
| 5,130,131 | 7/1992 | Narayanan et al. | 424/94.65 |
| 5,135,942 | 8/1992 | Dutzmann et al. | 514/383 |
| 5,139,774 | 8/1992 | Meinard et al. | 514/521 |
| 5,160,529 | 11/1992 | Scher et al. | 504/108 |
| 5,221,318 | 6/1993 | Fischer et al. | 504/283 |
| 5,223,526 | 6/1993 | McLoughlin et al. | 514/406 |
| 5,228,896 | 7/1993 | Misslitz et al. | 504/288 |
| 5,250,505 | 10/1993 | Kast et al. | 504/292 |
| 5,294,644 | 3/1994 | Login et al. | 514/698 |
| 5,310,721 | 5/1994 | Lo | 504/116 |
| 5,330,965 | 7/1994 | Misslitz et al. | 504/244 |
| 5,332,584 | 7/1994 | Scher et al. | 424/408 |
| 5,364,834 | 11/1994 | Kirchner et al. | 504/319 |
| 5,374,609 | 12/1994 | Kast et al. | 504/344 |
| 5,403,812 | 4/1995 | Kast et al. | 504/100 |
| 5,407,896 | 4/1995 | Kast et al. | 504/100 |
| 5,420,148 | 5/1995 | Dehne et al. | 514/395 |
| 5,433,173 | 7/1995 | Markles | 119/231 |
| 5,439,926 | 8/1995 | Dutzmann et al. | 514/383 |
| 5,446,067 | 8/1995 | Benoit et al. | 514/640 |
| 5,464,769 | 11/1995 | Attree et al. | 435/240.4 |
| 5,466,460 | 11/1995 | McMahon et al. | 424/408 |
| 5,508,249 * | 4/1996 | Narayanan et al. | 504/116 |

OTHER PUBLICATIONS

Koning; "Control of Flower Opening by Plant Hormones in *Gaillardia Grandiflora*"; (1981) 40–67; *Dissertation, University of Michigan*.

Lay–Yee, et al.; "Changes in Cotyledon mRNA during Ethylene Inhibition of Floral Induction in Pharbitis nil Strain Violet"; (1987) 84:545–548; *Plant Physiol*.

Lipe, et al; "Ethylene, a Regulator of Young Fruit Abscission"; (1973) 51:949–953; *Plant Physiol*.

Lipe, et al; "Ethylene: Role in Fruit Abscission and Dehiscence Processes"; (1972) 50:759–764; *Plant Physiol*.

Machackova, et al; "Reversal of IAA–Induced Inhibition of Flowering by Aminoethoxyvinylglycine in Chenopodium"; (1986) 4:203–209; *Journal of Plant Growth Regulation*.

Owens, et al; "Induction of Perfect Flowers on Gynoecious Muskmelon by Silver Nitrate and Aminoethoxyvinylglycine"; (1980) 15(5):654–655; *HortScience*.

Owens, et al; "Induction of Staminate Flowers on Gynoecious Cucumber by Aminoethoxyvinylglycine"; (1980) 15(3):256–257; *HortScience*.

Stanley, et at.; "The site of ethephon application and its effect on flower initiation and growth of chrysanthemum"; (1989) 64(3)341–350; *Journal of Horticultural Science*.

Suge; "Inhibition of photoperiodic floral induction in Pharbitis nil by ethylene"; (1972) 13:1031–1038; *Plant & Cell Physiol*.

van Altvorst, et al; "The role of ethylene in the senescence of carnation flowers, a review"; (1995) 16:43–53; *Plant Growth Regulation*.

van Doorn, et al; "Developments in the use of growth regulators for the maintenance of post–harvest quality in cut flowers and potted plants"; (1991) 298:195–208; *Acta Horticulturae*.

Veen, "Use of Inhibitors of Ehtylene Action", (1987) 201:213–222, *Acta Horticulturae*.

White et al: "Environmental control of ethylene biosynthesis", (1992) 147–155; *Progress in Plant Growth Regulation*.

Woltering et al: "Amino–oxyacetic acid: analysis and toxicology"; (1987) 216:273–280; *Acta Horticulturae*.

*Farm Chemicals Handbook '95*, Meister Publishing Company, Willoughby (Ohio), vol. 81, 1995, p. C13.

International Search Report for PCT/US 97/24177 dated May 22, 1998.

* cited by examiner

PLANT GROWTH REGULATORS IN PYRROLIDONE SOLVENTS

NOTICE OF COPENDING PATENT APPLICATIONS.

This application is a continuation-in-part of U.S. patent application Ser. No. 08/771,768 filed on Dec. 20, 1996, now abandoned. The following patent applications are copending in the United States Patent and Trademark Office with this application:
1) Plant Growth Retardants In Combination With Inhibitors Of Ethylene Biosynthesis Or Action, U.S. patent application Ser. No. 08/770,788, filed on Dec. 20, 1996 now U.S. Pat. No. 5,869,424, and incorporated herein by reference;
2) Low Rate Application of Inhibitors of Ethylene Biosynthesis or Action, U.S. patent application Ser. No. 08/770,492, filed on Dec. 20, 1996 now U.S. Pat. No. 5,834,403, and incorporated herein by reference;
3) Encapsulated Plant Growth Regulator Formulations, U.S. patent application Ser. No. 08/771,319, filed on Dec. 20, 1996 now U.S. Pat. No. 5,837,653, and incorporated herein by reference;
4) Encapsulated Plant Growth Regulator Formulations And Applications, U.S. patent application Ser. No. 08/771,734, filed on Dec. 20, 1996 now U.S. Pat. No. 5,861,360 and incorporated herein by reference;
5) Encapsulated Plant Growth Regulator Formulations In Combination With Plant Growth Retardants, U.S. patent application Ser. No. 08/771,769, filed on Dec. 20, 1996 now abandoned, and incorporated herein by reference;
6) Aminoethoxyvinylglycine in combination with a Plant Growth Regulator, U.S. patent application Ser. No. 08/777,716, filed on Dec. 20, 1996 now U.S. Pat. No. 5,935,906, and incorporated herein by reference.

FIELD OF THE INVENTION

The present invention is related generally to the field of agriculture and specifically to compositions and use of plant growth regulators.

BACKGROUND OF THE INVENTION

Agriculture workers actively seek ways to improve the economic output of commercial crops. For example, in cotton crops, workers seek to improve such growth factors as increased in boll set, increased floral initiation, decreased floral abscission, decreased boll abscission, increased germination, and enhanced root growth. Workers also seek to increase plant tolerance to environmental stress.

Formulations containing plant growth regulators (PGRs) have been developed to improve the economic yield of agricultural plants. Plant growth retardants and inhibitors of ethylene biosynthesis or action are two types of PGRs. Some plant growth retardants have been shown to inhibit gibberellin biosynthesis resulting in the reduction of shoot height in small grains and cotton. This reduction in shoot height has a strong economic benefit since it provides for less lodging in small grains and reduction of excessive vegetative growth. It also provides more uniform ripening in cotton.

Three groups of gibberellin biosynthesis inhibitors are known. The first group encompasses compounds with quaternary ammonium, phosphonium or sulphonium moieties. One example of a compound from this group is mepiquat chloride, described in U.S. Pat. No. 3,905,798 and incorporated herein by reference. Mepiquat chloride may increase cotton yields, boll load, lint yield and seed yield. Mepiquat chloride is also known to reduce vegetative growth, plant height and boll rot. Mepiquat chloride also induces early uniform ripeness if the plants are treated early during their development. Chlormequat chloride is also a representative compound of this group.

The second group of plant growth retardants encompasses compounds with a nitrogen containing heterocycle such as flurprimidol, paclobutrazol, uniconazole and ancymidol.

The third group encompasses acylcylcohexanediones (such as trinexapac-ethyl and prohexadione-Ca) and daminozide.

It is known that ethylene is involved in plant senescence and plant stress reactions. Ethylene is also involved in leaf, flower, and fruit abscission. Hence, agents that inhibit or regulate the production of ethylene or control its action in plants have been developed in an effort to improve the yield of agricultural crops. Inhibitors of ethylene biosynthesis include substituted oxime-ethers as described in U.S. Pat. No. 4,744,811, incorporated herein by reference. These compounds are also described in PCT Application WO 95-02211, incorporated herein by reference, as being soil amendment compositions that increase the assimilation of nitrogen by higher plants.

Other inhibitors of ethylene biosynthesis or action include aminoethoxyvinylglycine ("AVG"), aminooxyacetic acid ("AOA"), rhizobitoxine, and methoxyvinyl glycine ("MVG"). Silver ions (e.g. silver thiosulfate), and 2,5-norbornadiene inhibit ethylene action.

Plant growth regulators have also been used to protect crops from the effects of environmental stress. Gianfagna, T. J. et al. "Mode of Action and Use of Growth Retardants in Reducing the Effects of Environmental Stress on Horticultural Crops: Karssen C. N. et al. (eds.) *Progress in Plant Growth Regulation*, pp. 778–87 (1992). For example, researchers found that if ethephon was applied at a low rate (0.08 mM) it significantly delayed bloom in peach and reduced side effects. Researchers also found that ethephon increased the yields and hardiness of several horticultural plants.

Although PGRs have been developed as a means to improve agricultural crop yields, certain obstacles make the actual use of the PGR prohibitive. For example, many of the compounds display phytotoxicity. Other compounds are difficult to synthesize.

Many compounds require high rate applications to be effective. For example, PCT Application WO 93/07747, incorporated herein by reference, describes an improvement in a plant growth factor by applying aminoethoxyvinylglycine ("AVG"), an inhibitor of ethylene biosynthesis, to cotton plants. As the rate of AVG treatment increased, so did the improvement. (WO 93/07747, Examples 2–4). Assuming that a spray volume of 500 I/ha was used, the rates of application described in WO 93/07747 would be approximately 62.5 to 500 g ai/ha (ai—active ingredient). The maximum rate response occurs at the highest rates.

High rate applications may result in a significant waste of material and may result in the discharge of the PGRs into the surrounding environment. Also, although many of these compounds may induce a beneficial growth habit, they do not provide consistent improvement in plant growth factors. Other compounds may lose their effectiveness or cause a reduction in yield when applied to species which are under some form of environmental stress.

Encapsulated herbicides, pesticides and plant growth regulators have been described in the prior art. The use of interfacial polymerization to microencapsulate both water-soluble and water-insoluble materials using polymers is known. Others have described entrapped water-insoluble PGRs in starch. U.S. Pat. No. 4,382,813.

Polyvinyl alcohol (PVA) has been described as: a protective colloid in an emulsion formed by the dispersion of an organic solution containing a plant growth regulator, U.S. Pat. No. 5,160,529; as a dispersant in an oil-in-water emulsion, U.S. Pat. No. 4,871,766; as an ingredient in powders, granules or lattices, U.S. Pat. No. 4,486,218; and as an ingredient in oil-in-water emulsions having particles from 1 to 200 microns wherein the emulsion also contains a thickener, U.S. Pat. No. 4,283,415.

U.S. Pat. No. 4,997,642 discloses stable oil-in-water emulsions containing a PVA, a surfactant, a salt, and a water-insoluble oily compound, such as a plant growth regulator, wherein the compound is dispersed as a particle having an average size of less than one micron.

It is also been noted that octylpyrrolidone and dodecylpyrrolidone are of increasing importance in plant protection formulations. Emulsions are also commonly suggested for use in plant protection formulations.

Although these formulations provide unique benefits in the art, obstacles still are encountered by those of ordinary skill in the art in developing formulations that are stable and allow for the active ingredient of the formulation to provide beneficial results when used for its intended purpose. Obstacles still remain in providing formulations that provide a suitable solution for an active agent such as an ethylene inhibitor wherein the active ingredient remains stable and provides its appropriate benefit to crops.

Hence, it is an object of this invention to not only provide a stable formulation, but one that also provides for a stable active compound in solution. It is also an object of the invention to provide a composition that allows for an increase in the activity of ethylene inhibitors.

SUMMARY OF THE INVENTION

Provided herein is a composition comprising a plant growth regulator, octylpyrrolidone, and an emulsifier. The emulsifier may be provided in combination with an ethylene oxide block polymer. Also provided herein is a method of improving a plant growth factor in a plant comprising administering to said plant a composition comprising a plant growth regulator, octylpyrrolidone, and an emulsifier. Still further provided is a method of increasing ethylene inhibition of an ethylene inhibitor comprising administering to said plant a composition comprising a plant growth regulator, octylpyrrolidone, and an emulsifier.

An improvement in a plant growth factor is defined as an agronomic improvement of plant growth such as increased floral (square) initiation, increased flower retention, increased fruit retention, increased square retention, increased boll retention, increased root growth, decreased internode length, increased stress tolerance, decreased wilting, decreased senescence, darker green pigmentation, increased germination rate, increased tolerance to low and high temperatures, and increased crop yield. That is, a favorable alteration of the physiology or growth of plants or an increase or decrease in plant growth which leads to an economic or agronomic benefit. Improvement in growth factors that result from the inhibition of ethylene production is preferred. The emulsifier comprises a blend of nonyl phenol ethoxylate and dioctyl sulfosuccinate.

DETAILED DESCRIPTION OF THE INVENTION

The emulsions of the present invention are particularly suitable for formulations containing PVA encapsulated inhibitors of ethylene biosynthesis or action, preferably substituted oxime-ethers having the formula:

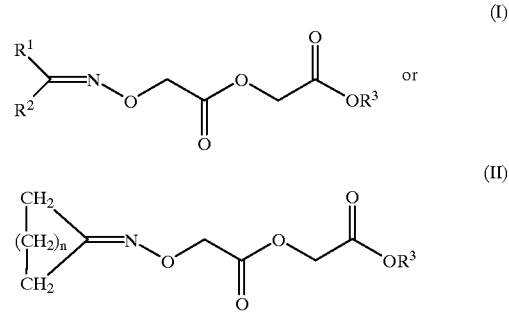

where R1 and R2 independently of one another are C1–C6-alkyl, n is 2 or 3 and R3 is hydrogen or C1–C6 alkyl.

Examples of other compounds that may be used include [((isopropylidene)-amino]oxy acetic acid represented by the structure:

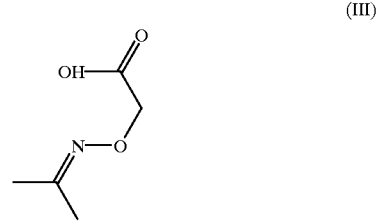

Another example of a compound that may used in the present invention is aminooxyacetic ("AOA") acid represented by the following structure:

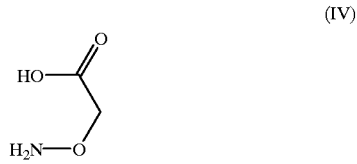

Preferred oxime-ethers for use in the formulations include the following compounds:

1) {[(isopropylidene)-amino]oxy}-acetic acid-2-(methoxy)-2-oxoethyl ester represented by the structure:

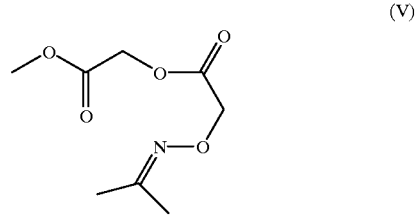

2) {[(isopropylidene)-amino]oxy}-acetic acid-2-(hexyloxy)-2-oxoethyl ester represented by the structure:

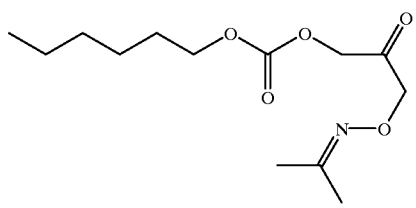

and 3) {{cyclohexylidene)-amino]oxy}-acetic acid-2-(isopropyloxy)-2-oxyethyl ester (methoxy)-2-oxoethyl ester represented by the structure:

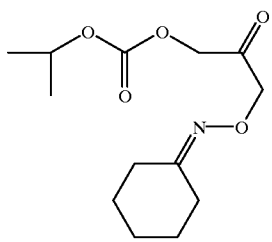

The most preferred compound for carrying out the present invention comprises {[(isopropylidene)-amino]oxy}-acetic acid-2-(methoxy)-2-oxoethyl ester.

Other compounds that may be used in the invention include aminoethoxyvinylglycine and methoxyvinyl glycine.

A preferred emulsifier for use in the current invention is a blend comprising dioctyl sulfosuccinate and nonyl phenol ethoxylate. Other emulsifiers that may be used comprise ethoxylated castor oils, nonyl phenolethoxylates, sulfosuccinates, and organic phosphoric acid esters. Surface agents may also be used such as nonionic agents, for example condensation products of alkyl substituted phenol with ethylene oxide; fatty esters of polyhydric alcohol ethers (sorbitan fatty acid esters); and condensation products of such esters with ethylene oxide (e.g. polyoxyethylene sorbitan fatty acid esters, block copolymers of ethylene oxide, polyethylene oxide); acetylenic glycols and ethoxylated acetylenic glycols. Cationic surfactants that may be used comprise quaternary ammonium salts which contain, as N-substituents, at least one polyglycol ether or $C_8$–$C_{22}$ alkyl radical and as further substituents, lower hydroxyalkyl radicals. The salts are preferably in the form of halides, methylsulfates, or ethylsulfates, stearyltrimethylammonium chloride, etc.

The ethylene inhibitors are preferably provided in the composition in a range, of the total weight of the composition, of about 1% to about 60%, most preferably at about 5%. The octylpyrrolidone is preferably provided in a range, of the total weight of the composition, of about 5% to about 95%, preferably at about 83%. When an emulsifier is provided in combination with a surface agent (to form an emulsification system) it is preferably provided in a range, of the total weight the composition, of about 1% to about 20%. Preferably, a block copolymer is provided in the composition in a range, of the total weight of the composition, of 1% to 10%, preferably at about 8. The emulsifier is preferably is provided in range, of the total weight of the composition, of about 1% to 10%, preferably at about 4%.

Depending on the solvent system used and the active ingredient to be formulated, suitable surface-active compounds can be selected and used to carry out the invention. For example, suitable where nonionic, cationic, or anionic surfactants having good emulsifying and wetting properties will be used.

Anionic surfactants comprising either water-soluble soaps, water-soluble synthetic surface-active compounds or blends may be used in the present invention. Also, soaps are the alkali, alkaline earth metal salts, or unsubstituted or substituted ammonium salts of higher fatty acids ($C_{10}$–$C_{20}$), the sodium salts of oleic or stearic acid, or of natural fatty acid mixtures obtained from coconut oil, tallow oil, or fatty acid methyltautrin salts may also be used.

Synthetic surfactants may also be used, including fatty sulfonates, fatty sulfates, sulfonated benzimidazole derivatives or alkylarylsulfonates. The fatty sulfonates or sulfates are prefereably the alkali, alkaline earth metal salts, or unsubstituted or substituted ammonium salts containing a C8–C22 alkyl radical; e.g., the sodium or calcium salts of lignosulfonic acids, of dodecysulfate or a mixture of fatty alcohol sulfates obtained from natural fatty acids. These compounds may also comprise the salts of sulfuric acid esters and sulfonic acids of fatty alcohols/ethylene oxide adducts. The sulfonated benzimidazole derivative preferably contain 2 sulfonic acid groups and one fatty acid radical containing 8 to 22 carbon atoms. Examples of alkylarylsulfonates are the sodium, calcium, or triethanolamine salts of dodecylbenzenesulfonic acid, dibutyinaphthalenesulfonic acid, or a naphthalenesulfonic acid/formeldehyde condensation product. Also suitable for use in the present invention are corresponding phosphates, or salts of the phosphoric acid ester of an adduct of p-nonylphenol with 4 to 14 moles of ethylene oxide. Suitable anionic emulsifiers may also include sulfosuccinate chemistries.

Non-ionic surfactants that may be used are preferably polyglycol ether derivatives of aliphatic or cycloaliphatic alcohols, or saturated or unsaturated fatty acids, and alkyphenols containing 3 to 30 glycol ether groups and 8 to 20 carbon atoms in the aliphatic hydrocarbon moiety and 6 to 18 carbon atoms in the alkyl moiety of the alkylphenol.

Other suitable non-ionic surfactants that may be used in the present invention are the water soluble adducts of polyethylene oxide with polypropylene glycol, and alkylpolypropylene glycol.

Other representative examples of nonionic surfactants are nonylphenol-polyethoxyethanols.

Preferred formulations of the invention also provide a significant benefit in that they produce a significant improvement in a plant growth factor when applied at low rate. Low rate application is defined as a single application rate lower than about 50 g ai/ha (grams of active ingredient per hectare). An effective number of low rate applications can be made throughout the growing season. Preferably, the low rate application is performed from one to about ten times during the growing season, most preferably from one to about four times during the growing season. Preferred embodiments of the present invention comprise single application rates ranging from about 100 mg ai/ha to about 50 g ai/ha applied from one to four times during a growing season and ranging from about 500 mg ai/ha to about 10 g ai/ha applied from one to four times during a growing season. Other rates useful for carrying-out the invention include a rate of less than or equal to about 2 g ai/ha and down to about 100 mg ai/ha applied from one to four times during a growing season. The most preferred single application rate is about 500 mg/ha to about 1.5 g ai/ha applied from one to four times during a growing season.

The present invention finds its best results in horticultural and agricultural plants and crops. The invention provides most consistent improvement of at least one plant growth factor in the following plants: cotton, soybean, peanut, pepper, tomato, wheat, barley, rice plant, apple, citrus, grape, corn and canola. Improvement is also found in turf.

The formulations described in this invention are generally applied to the foliage prior to bud and flower development but they can also be applied to the foliage, buds, flowers, or fruits beginning at early bud development (e.g., matchhead square in cotton) in one to four sequential applications. If sequential applications are used, applications are preferably timed at approximately 10 to 14 days apart. When applied by spraying, the active ingredient is generally mixed with water as a carrier solution in a dilution sufficient to cover the area. Typically the spray volume of the aqueous treatment solution would be about 150 to 500 I/ha for arable crops and up to about 1,500 I/ha fruit trees. Soil drenching is another method of application that is useful when practicing the invention.

Another aspect of the present invention is that the compositions and methods of carrying out the invention may be used in combination with plant growth regulators such as mepiquat chloride (Pix ® plant growth regulator"). Mepiquat chloride may be applied either alone or in combination with the compositions preferably at a rate of 12 to 200 g ai/ha. When applied in combination, the combination may be applied using the same "tank-mix" spray solution. However, combinations of mepiquat chloride and the compositions of the present invention may also include separate applications made within 72 hours of each other on the same plants.

Accordingly, the present invention provides a method which improves the economic or agronomic output of agricultural crops and decreases the amount of material that needs to be used to obtain improvement in a plant growth factor.

Surprising and unexpectedly, the present invention not only provides for a composition that is stable but one that provides superior ethylene inhibition.

The following examples are illustrative only and are not meant to limit the invention in any manner.

EXAMPLE 1

A composition containing {[(isopropylidene)-amino] oxy}-acetic acid-2-(methoxy)-2-oxoethyl ester (99% Technical Grade, BASF Corporation) in a solvent having an emulsifier system was prepared. A C8 pyrrolidone solvent (AGSOLEX® 8, 1-octylpyrrolidone, ISP) was mixed with an emulsifier System containing a block copolymer (PLURAFAC® LF-700, BASF Corporation) and an emulsifier comprising a blend of 80% nonyl phenol ethoxylate (MAKON®, Stepan Chemical) and 20% dioctyl sulfosuccinate (AERSOL® OT 100). The resulting solution was mixed until a clear homogenous solution was formed. {[(isopropylidene)-amino]oxy}-acetic acid-2-(methoxy)-2-oxoethyl ester (99% Technical Grade, BASF Corporation) was added to the clear solution and mixed until a clear homogenous solution was formed. The resulting composition contained about 82.6% C8 pyrrolidone, about 8.3% block copolymer emulsifier, about 4.1% of the emulsifier and about 5.0% of the {[(isopropylidene)-amino]oxy}-acetic acid-2-(methoxy)-2-oxoethyl ester. This resulting composition was mixed with PIX® mepiquat chloride plant growth regulator (BASF Corporation) such that the mepiquat chloride was applied to cotton in field studies at a rate of 12 g/ha and the {[(isopropylidene)-amino]oxy}-acetic acid-2-(methoxy)-2-oxoethyl ester contained in the solvent with an emulsifier system was applied at 1 and 10 g/ha. The results are displayed in Table 1.

TABLE I

| (Cotton) | | | |
|---|---|---|---|
| Yield | | | |
| Rate (g/ha) | 1 | 10 | mc |
| Relative Yield (% compared to untreated)) | 103% | 106% | 102% |
| Frequency of Positive Yield | 62% | 62% | 38% | mc = mepiquat chloride

The results show that the treated plants had a 3% and 6% increase over the untreated plants at 1 and 10 g/h rates respectively—with a frequency of positive yield of 62%.

EXAMPLE 2

Formulations of the present invention were prepared as described in Example 1 and were tested for hydrolysis half-life. For example, the half-life of {[(isopropylidene)-amino]oxy}-acetic acid-2-(methoxy)-2-oxoethyl ester (99% Technical Grade, BASF) in water at 25° C. ranges from 12 days to about 21 days with increasing pH (from about 3 to 8). Polyvinyl alcohol encapsulated formulations had a hydrolysis half-life (25° C.) ranging from 32 to about 50 days. The octylpyrrolidone formulations described in Example 1 had a half-life of about 462 days in aqueous solutions at 25° C. When compared to other pyrrolidones such as dodecylpyrrolidone, the octylpyrrolidone formulation was about four times more stable. Formulations prepared with methylpyrrolidone had a high degree of stability (over 7,000 days) but showed no ethylene inhibition.

When the stability of the compositions were tested in barley leaves for ethylene inhibition it showed very strong inhibition using the following rating scale:

−=induction of ethylene formation
0=no effects observed
+=weak inhibition of ethylene formation
++=intermediate inhibition of ethylene formation
+++=strong inhibition of ethylene formation
++++ =very strong inhibition of ethylene formation Other important observations indicated that a 40 μl droplet of a 1% volume dilution of the formulation of the present invention described in Example 1 applied to a cotton leaf gave rise to a softened and swelled leaf, indicating that the formulation may have uptake characteristics. A methylpyrrolidone formulation applied to a cotton leaf gave rise to a liquid phase that remained on the surface of the leaf, with no noticable effect on uptake. A dodecylpyrrolidone formulation applied to a cotton leaf gave rise to a damaged burned leaf surface; ethylene formation was deduced.

The invention has been described with reference to various specific embodiments. However, many variations and modifications may be made while remaining within the scope and spirit of the invention.

What is claimed is:

1. A composition for inhibiting ethylene production in plants comprising: an ethylene biosynthesis inhibitor; octylpyrrolidone; and an emulsifier.

2. The composition as recited in claim 1 wherein the ethylene biosynthesis inhibitor comprises a substituted oxime-ether of the formula:

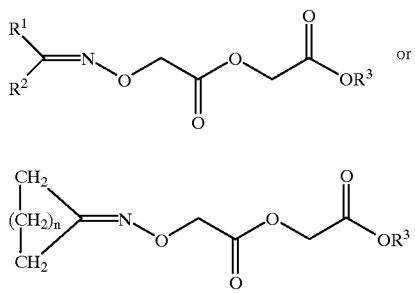

where R1 and R2 independently of one another are C1–C6-alkyl, n is 2 or 3 and R3 is hydrogen or C1–C6-alkyl.

3. The composition as recited in claim 2 wherein the oxime-ether is selected from the group consisting of {[(isopropylidene)-amino]oxy}-acetic acid-2-(methoxy)-2-oxoethyl ester, {[(isopropylidene)-amino]oxy}-acetic acid-2-(hexyloxy)-2-oxoethyl ester, and {{cyclohexylidene)-amino]oxy}-acetic acid-2-(isopropyloxy)-2-oxyethyl ester-(methoxy)-2-oxoethyl ester.

4. The composition as recited in claim 2 wherein the substituted oxime-ether comprises {[(isopropylidene)-amino]oxy}-acetic acid-2-(methoxy)-2-oxoethyl ester.

5. The composition of claim 1 wherein said emulsifier includes at least one compound selected from the group consisting of:
ethylene oxide block polymers;
nonyl phenol ethoxylate;
dioctyl sulfosuccinate; and
mixtures thereof.

6. The composition of claim 2 wherein said emulsifier includes at least one compound selected from the group consisting of:
ethylene oxide block polymers;
nonyl phenol ethoxylate;
dioctyl sulfosuccinate; and
mixtures thereof.

7. The composition of claim 3 wherein said emulsifier includes at least one compound selected from the group consisting of:
ethylene oxide block polymers;
nonyl phenol ethoxylate;
dioctyl sulfosuccinate; and
mixtures thereof.

8. The composition of claim 4 wherein said emulsifier includes at least one compound selected from the group consisting of:
ethylene oxide block polymers;
nonyl phenol ethoxylate;
dioctyl sulfosuccinate; and
mixtures thereof.

9. The composition of claim 5 wherein said emulsifier comprises a blend of nonyl phenol ethoxylate and dioctyl sulfosuccinate.

10. The composition of claim 6 wherein said emulsifier comprises a blend of nonyl phenol ethoxylate and dioctyl sulfosuccinate.

11. The composition of claim 7 wherein said emulsifier comprises a blend of nonyl phenol ethoxylate and dioctyl sulfosuccinate.

12. The composition of claim 8 wherein said emulsifier comprises a blend of nonyl phenol ethoxylate and dioctyl sulfosuccinate.

13. A method of increasing ethylene inhibition of an ethylene inhibitor comprising administering to said plant a composition comprising an ethylene biosynthesis inhibitor; 1-octylpyrrolidone; and an emulsifier.

14. The method of claim 13 wherein the ethylene biosynthesis inhibitor comprises a substituted oxime-ether of the formula:

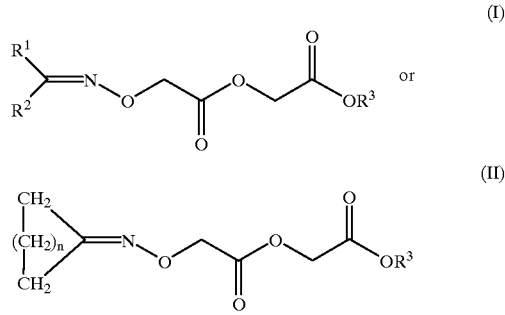

where R1 and R2 independently of one another are C1–C6-alkyl, n is 2 or 3 and R3 is hydrogen or C1–C6-alkyl.

15. The method as recited in claim 14 wherein the oxime-ether is selected from the group consisting of {[(isopropylidene)-amino]oxy}-acetic acid-2-(methoxy)-2-oxoethyl ester, {[(isopropylidene)-amino]oxy}-acetic acid-2-(hexyloxy)-2-oxoethyl ester, and {{cyclohexylidene)-amino]oxy}-acetic acid-2-(isopropyloxy)-2-oxyethyl ester-(methoxy)-2-oxoethyl ester.

16. The method as recited in claim 15 wherein the substituted oxime-ether comprises {[(isopropylidene)-amino]oxy}-acetic acid-2-(methoxy)-2-oxoethyl ester.

17. The method of claim 13 wherein said emulsifier includes at least one compound selected from the group consisting of:
ethylene oxide block polymers;
nonyl phenol ethoxylate;
dioctyl sulfosuccinate; and
blends thereof.

18. The method of claim 14 wherein said emulsifier includes at least one compound selected from the group consisting of:
ethylene oxide block polymers;
nonyl phenol ethoxylate;
dioctyl sulfosuccinate; and
blends thereof.

19. The method of claim 15 wherein said emulsifier includes at least one compound selected from:
ethylene oxide block polymers;
nonyl phenol ethoxylate;
dioctyl sulfosuccinate; and
blends thereof.

20. The method of claim 16 wherein said emulsifier includes at least one compound selected from:

ethylene oxide block polymers;

nonyl phenol ethoxylate;

dioctyl sulfosuccinate; and blends thereof.

21. The method of claim 17 wherein the emulsifier comprises a blend of nonyl phenol ethoxylate and dioctyl sulfosuccinate.

22. The method of claim 18 wherein the emulsifier comprises a blend of nonyl phenol ethoxylate and dioctyl sulfosuccinate.

23. The method of claim 19 wherein the emulsifier comprises a blend of nonyl phenol ethoxylate and dioctyl sulfosuccinate.

24. The method of claim 20 wherein the emulsifier comprises a blend of nonyl phenol ethoxylate and dioctyl sulfosuccinate.

* * * * *